United States Patent [19]

Wong et al.

[11] Patent Number: 5,795,749
[45] Date of Patent: Aug. 18, 1998

[54] USE OF 2-DEOXYRIBOSE-5-PHOSPHATE ALDOLASE TO PREPARE 2-DEOXYFUCOSE, ANALOGUES AND DERIVATIVES

[75] Inventors: Chi-Huey Wong, Rancho Sante Fe, Calif.; Harrie J. M. Gijsen, Er Roemond, Netherlands

[73] Assignee: The Scripps Research Institution, LaJolla, Calif.

[21] Appl. No.: 416,999

[22] Filed: Apr. 5, 1995

[51] Int. Cl.$^6$ .................. C12P 19/02; C12P 11/00; C12P 19/00; C07H 1/00
[52] U.S. Cl. .................. 435/105; 435/72; 435/130; 536/1.11; 536/18.7; 536/124
[58] Field of Search .................. 435/72, 105, 130; 536/1.11, 18.7, 124

[56] References Cited

U.S. PATENT DOCUMENTS

| | | | |
|---|---|---|---|
| 5,079,353 | 1/1992 | Ratcliffe et al. | 536/53 |
| 5,276,120 | 1/1994 | Wong et al. | 546/184 |
| 5,296,594 | 3/1994 | Ratcliffe et al. | 536/53 |

OTHER PUBLICATIONS

Gijsen et al, J. Am. Chem. Soc. 116(18): 8422–8423 (1994).
Chou et al, J. Am. Chem. Soc. 116 (14): 6191–6194 (1994).
Barbas et al, J. Am. Chem. Soc. 112(5): 2013–2014 (1990).
Wong et al. J. Am. Chem. Soc. 117(12) 3333–3339 (1995).
Phillips et al., *Science*, 250:1130–1132 (1990).
Walz et al. *Science*, 250:1132–1135 (1990).
Wong et al., *Enzymes in Synthetic Organic Chemistry*, Pergamon, Oxford (1994) Chapter 4.
Barbas et al. *J. Am. Chem. Soc.*, 112:2013–2014 (1990).
Chen et al., *J. Chem. Soc.*, 114:741–747 (1992).
Gijsen et al., *J. Am. Chem. Soc.*, 116:8422–8423 (1994).
Henderson et al. *J. Am. Chem. Soc.*, 116:558–561 (1994).
Effenberger et al., *Tetrahedron Lett.* 33(36):5157–5160 (1992).
Chou et al., *J. Am. Chem. Soc.* 117:2947–2948 (1995).
Gijsen et al., *J. Am. Chem. Soc.* 117:2947–2948 (1995).

*Primary Examiner*—Francisco C. Prats
*Attorney, Agent, or Firm*—Welsh & Katz, Ltd.

[57] ABSTRACT

Processes using 2-deoxyribose-5-phosphate aldolase (DERA) are described for the preparation of 2-deoxyfucose and related compounds. In one embodiment, DERA is used to catalyze the condensation of acetaldehyde as donor and a 2(R)-hydroxy-3-(hydroxy or mercapto)-propionaldehyde derivative to form a 2-deoxysugar whose hydroxyls have the configuration of fucose. In another embodiment, DERA is used to catalyze the condensation of two moles of acetaldehyde as donor and one mole of a 2-substituted acetaldehyde acceptor to form a 2,4,6-trideoxyhexose via a 4-substituted-3-hydroxybutanal intermediate.

16 Claims, No Drawings

USE OF 2-DEOXYRIBOSE-5-PHOSPHATE ALDOLASE TO PREPARE 2-DEOXYFUCOSE, ANALOGUES AND DERIVATIVES

GOVERNMENT RIGHTS

This invention was made with government support under Contract No. GM 44154 by the National Institutes of Health. The government has certain rights in the invention.

TECHNICAL FIELD

The present invention relates to the synthesis of carbohydrate molecules, and particularly to the synthesis of compounds related to 2-deoxyfucose.

BACKGROUND ART

2-Deoxy-L-fucose (2,6-dideoxy-L-galactose) is a constituent of rhodomycins, cinerubins A and B, the antibiotic azalomycins-B [Horton et al., Method's Carbohydr. Chem., 8:201(1980) and the citations therein] and the anthracycliens [Florent et al., J. Med. Chem., 36:1364(1993)]. L-Fucose is a constituent of sialyl Lewix X,and sialyl Lewis A molecules that are involved with cellular adhesion mediated by the E- and P-selectins [Phillips et al., Science, 250:1130(1990); Walz et al, Science, 250:1132(1990); U.S. Pat. Nos. 5,079, 353 and 5,296,594; Berg et al., Biochem. Biophys. Res. Commun., 184:1048(1992), Berg et al. J. Biol. Chem., 23:14869(1991)].

Aldolases are a group of enzymes which catalyze C—C bond formation, often in a highly stereoselective way. Over thirty aldolases have been identified so far and several have been used in organic synthesis. [Wong et al., Enzymes in Synthetic Organic Chemistry, Pergamon, Oxford (1994) Chapter 4.] The mild reaction conditions, high stereoselectivity, and the minimal use of protective group chemistry make the use of aldolases an interesting alternative to the chemical aldo reactions. Most aldolases catalyze the condensation of an aldehyde with a ketone donor, giving a ketone as product. The enzyme 2-deoxyribose-5-phosphate aldolase (DERA, EC 4.1.2.4) [Barbas et al., J. Am. Chem. Soc., 112:2013 (1990); Chen et al., J. Am. Chem. Soc., 114:741 (1992); Wong et al., J. Am. Chem. Soc., 117: (1995) in press; Gijsen et al., J. Am. Chem. Soc., 116:8422 (1994)].

In view of the importance of fucose and 2-deoxyfucose and their related compounds (analogues and derivatives), it would be of importance to be able to prepare such compounds with relative ease. The disclosures that follow describe several such synthesis that utilize the enzyme 2-deoxyribose-5-phosphate aldolase.

BRIEF SUMMARY OF THE INVENTION

One aspect of the invention contemplates the use of 2-deoxyribose-5-phosphate aldolase (DERA) to prepare a pentose product of Formula I

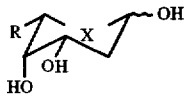

wherein X is O or S, and R is selected from the group consisting of hydrogen, $C_1$–$C_4$ alkyl and phenyl. That process comprises the steps of:

(a) admixing an aldehyde of Formula II

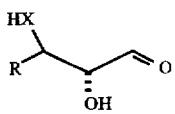

wherein X and R are as defined above, with acetaldehyde and DERA in an aqueous medium having a pH value of about 6.5 to about 8.5 and at a temperature of about 5° C. to about 45° C. to form a reaction mixture.

(b) That reaction mixture is maintained at that temperature and pH value for a time period sufficient for the product to form.

(c) The product is then recovered.

A particularly preferred aspect of the above process uses 2-deoxyribose-5-phosphate aldolase (DERA) to prepare a 2-deoxy-5-substituent-L-lyxo-pentose product in which the 5-substituent is $C_1$–$C_4$ alkyl or phenyl. That process comprises the steps of:

(a) admixing an aldehyde of Formula III

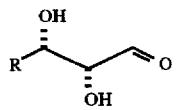

wherein R is $C_1$–$C_4$ alkyl or phenyl, with acetaldehyde and DERA in an aqueous medium at a pH value of about 7 to about 8 and at a temperature of about 15° C. to about 35° C. to form a reaction mixture in which acetaldehyde is in stoichiometric excess over the aldehyde of Formula III.

(b) The reaction mixture set forth is maintained in the absence of light at that temperature and pH value for a time period sufficient for the product to form.

(c) The product is then recovered.

Another aspect of this invention is a "one pot" synthesis of a 2,6-dideoxy hexose that is also a fucose derivative. This process uses 2-deoxyribose-5-phosphate aldolase (DERA) in a single vessel for the synthesis of a product compound of Formula V

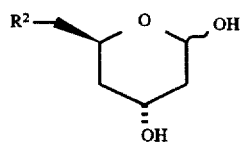

wherein $R^2$ is selected from the group consisting of hydrogen, $C_1$–$C_4$ alkoxy, halo and azido groups. Here, the process comprises the steps of:

(i) admixing the following materials in an aqueous medium at a pH value of about 6.5 to about 8.5 and at a temperature of about 5° C. to about 45° C. in a single reaction vessel to form a reaction mixture:

(a) acetaldehyde donor;

(b) $R^2$-substituted acetaldehyde acceptor; and (c) DERA wherein the molar ratio of donor to acceptor is about 2:1 to about 4:1 and DERA is present in an amount of about 125 to about 150U per millimole of the donor and acceptor combined.

(ii) The admixture is maintained at that temperature and pH value for a time period sufficient for the product compound to form.

(iii) The product compound is then recovered.

DETAILED DESCRIPTION OF THE INVENTION

One aspect of the invention contemplated the use of 2-deoxyribose-5-phosphate aldolase (DERA) in a process to prepare a pentose product of Formula I, below, whose R group, when other than hydrogen, and hydroxyls are in the stereochemical configuration of L-fucose.

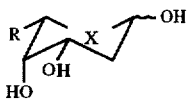

I

In Formula I, R is selected from the group consisting of hydrogen, $C_1$–$C_4$ alkyl and phenyl and X is S (sulfur) or O (oxygen).

In accordance with the process of this aspect of the invention, an aldehyde of Formula II, below, where R and X are as above,

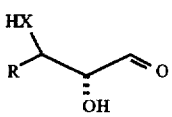

II is admixed with acetaldehyde and DERA in an aqueous medium at a pH value of about 6.5 to about 8.5 and at a temperature of about 5° C. to about 45° C. to form a reaction mixture.

That reaction mixture is maintained at the recited pH value and temperature for a time period sufficient for the product of Formula I to form, and that product is thereafter recovered.

This process is illustrated generally in the top line of Scheme 1, below, and more specifically in the following two lines, wherein Compounds 2a, 2b and 4 are shown to be prepared from compounds of Formulas III (Compounds 1a and 2b) and IV (Compound 3). Product yields are shown adjacent to the products.

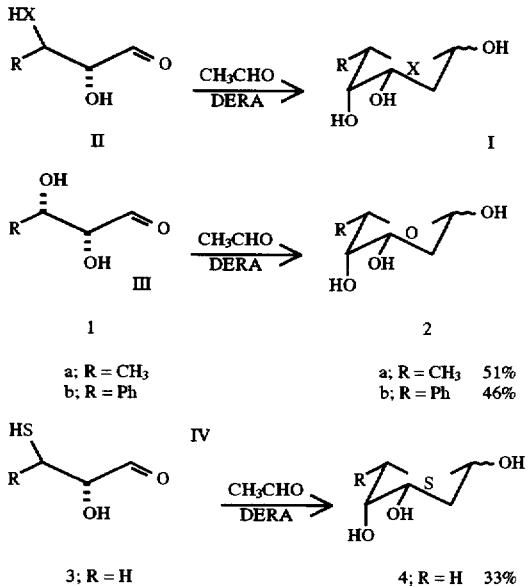

Acetaldehyde is often referred to herein and in the art as the donor substrate, and the second aldehyde (Formula II) is the acceptor substrate, or more simply as donor and acceptor. It is preferred that the acetaldehyde be in stoichiometric excess over the acceptor. The ratio of donor to acceptor is typically about 1.5:1 to about 5:1 on a molar basis, and more preferably at about 2.5:1 to about 4:1.

The pH value noted before of the reaction mixture is typically between about 6.5 and about 8.5, and is more preferably about 7.0 to about 8.0. A pH value of about 7.3 is most preferred. It is also preferred that the pH value of the initially formed reaction mixture be the same during the maintenance step; i.e., within about 0.2 pH units of each other, but this preference is not critical.

The process is also preferably carried out in the absence of light; i.e., in the dark. The components are thus admixed in the light, and the resulting reaction mixture is shielded from the light by any convenient means. The process is also preferably carried out in the absence of oxygen so the process is typically carried out in an atmosphere of nitrogen, argon or a similar gas.

Turning now to the reactants, acetaldehyde ($CH_3CHO$) is one reactant that is a donor in that acetaldehyde provides a carbanion that donates its pair of electrons in forming a covalent bond with the carbonyl carbon of the acceptor aldehyde of Formula II.

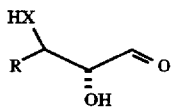

II

The compound of Formula II is shown with particular stereochemistry of the hydroxyl group of the carbon adjacent to the carbonyl group. That 2-position carbon thus has an R configuration. The configuration at the 3-position is not defined inasmuch as the R group can be hydrogen. However, when an R group is other than hydrogen, the configuration of the 3-position carbon is preferably S so that as shown, both the OH and XH groups extend below the plane of the page and can be shown using a dashed-wedge bond, as at position 2.

The configuration of the 3-position carbon atom quite unexpectedly plays some role in the rate of the aldol condensation reaction even though the bond that is formed is at the 1-position, two atoms removed. Thus, it was reported [Chen. et al., J. Am. Chem. Soc., 114:741(1992)] that a compound having a 2R,3S configuration and a terminal hydroxyl group exhibited a relative rate of zero when reacted with acetaldehyde in the presence of DERA, whereas an isomeric compound with a 2R,3R configuration exhibited a relative rate of 0.3 under conditions in which dihydroxyacetone phosphate exhibited a relative rate of 100. Thus, whereas the Chen et al., paper could be taken to suggest that no reaction would take place here, relatively high yield reactions were found here, as noted in Scheme 1.

Exemplary $C_1$–$C_4$ alkyl R groups include methyl, ethyl, propyl, isopropyl, butyl and sec-butyl. Methyl is a preferred R group when X is O, whereas hydrogen is a preferred R group when X is S.

The acceptor aldehydes have the preferred Formulas III and IV when X is O and S, respectively. These structural formulas are shown below.

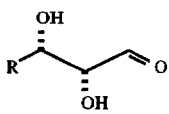

III

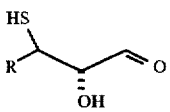

The amount of DERA utilized in these reactions can be very broad such as about 80 to about 100 or more units (U) of enzyme per millimole of combined donor and acceptor aldehydes. Use of greater amounts of enzyme do not increase the yield of products. It is preferred to use about 90 to about 100U of enzyme per millimole of combined aldehydes, with those aldehydes being present at a before-stated ratio.

Another contemplated aspect of this invention is the use of DERA to carry out multiple condensation reactions, and more particularly, three condensations. These reactions were first reported in Gijsen et al., *J. Am. Chem. Soc.*, 116: 8422 (1994). The general reaction is illustrated in Scheme 2, below, wherein $R^2$ is selected from the group consisting of hydrogen, $C_1$–$C_4$ alkoxy, halo and azido.

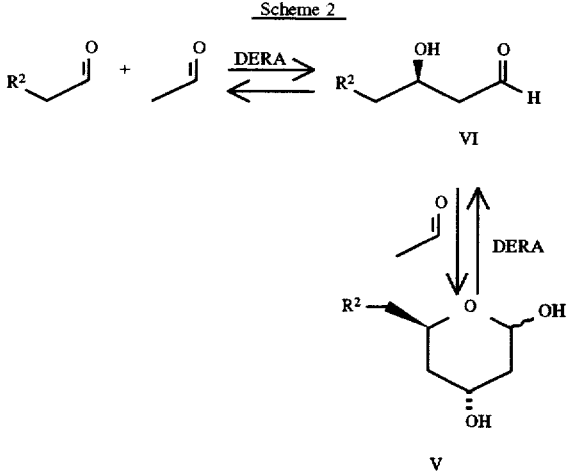

In Scheme 2, it is seen that one mole of an $R^2$-containing acetaldehyde derivative acceptor condenses with one mole of acetaldehyde as donor in a DERA-catalyzed reaction to form the 4-substituted-3-hydroxybutanal of Formula IV. That molecule then acts as acceptor for another mole of acetaldehyde as donor in a DERA-catalyzed condensation to form a compound of Formula V that is subsequently recovered.

It is believed that a multiple condensation as shown in Scheme 2 occurs here, but not in the previously discussed reactions because the β-hydroxyaldehyde of Formula IV cannot readily form a hemiacetal, which formulation effectively removes the hemiacetal from the reaction. Thus a compound of Formula II (i.e., a compound of Formulas III or IV) can form such an acetal.

In the above scheme, an exemplary $C_1$–$C_4$ alkoxy group includes methoxy, ethoxy, iso-propoxy and butoxy groups, whereas an exemplary halo group includes fluoro, chloro, bromo and iodo groups, with chloro being preferred.

A compound such as 2,4-dideoxyfucose formed where $R^2$ is hydrogen is an intermediate used in the preparation of compactin, a cholesterol-lowering drug. The 2,4-dideoxyfucose is oxidized to the lactone that is a derivative of mevinic acids that are HMG-CoH reductase inhibitors.

A process contemplated here is carried out as described before for the first-mentioned process for using DERA, with two exceptions.

A first exception is the molar ratio of acetaldehyde donor to $R^2$-substituted acetaldehyde acceptor. Inasmuch as two moles of acetaldehyde are consumed here, that ratio is preferably about 2:1 to about 4:1 on a molar basis.

A second exception is that the DERA is used in a larger amount to improve yield of the 2,4,6-trideoxy hexose product of Formula V. Thus, DERA is used here at about 125 to about 150 or more units per millimole of the combined donor and acceptor aldehydes used at an above-discussed molar ratio.

Results and Discussion

*E. coli* cells from the strain DH5α (ATCC 86968), transformed with the plasmid pVH17 containing the DERA gene, were used to provide about 124,000U of DERA per 6L of culture. Using lysozyme provided a convenient method for obtaining cell-free extracts, and is comparable to the disruption of the cells in a French Press (~1600 U/g of cells) [Barbas, et al., *J. Am. Chem. Soc.*, 112:2013 (1990)]. The lysozyme method was especially useful when processing a large volume of cells. A net increase of 251 percent in the recovered activity was obtained after ammonium sulfate precipitation, salt removal and buffer exchange, compared to only about 30 percent recovered activity after overnight dialysis using tubing with a molecular weight cut off of 5000.

This new strategy for purification was based on the further use of anion exchange chromatography and chromatofocusing. Scale-up of the anion exchange chromatography was relatively easy as DERA was eluted in the void volume. Further purification by chromatofocusing using a pH gradient from 6 to 4 gave a main peak corresponding to DERA which upon analysis by SDS-PAGE revealed a single band of 28 kD. However, further analysis by isoelectrofocusing (IEF) revealed the existence of two more proteins. A narrower pH range (5.5-4.5) was used, and the peak containing DERA activity was analyzed by SDS-PAGE and IEF. A single band was obtained in both cases.

This is the first reported purification to homogeneity of 2-deoxyribose-5-phosphate aldolase that is especially noteworthy as the purification sequence produced an overall yield of 83 percent. For crystallization, DERA was dialyzed against Tris-HCl and concentrated to 10 mg/mL; crystals were immediately obtained upon treatment with polyethylene glycol [Wong et al., *Enzymes in Synthetic Organic Chemistry*, Pergamos, Oxford (1990) Chapter 4].

It was found that using DERA after the ammonium sulfate precipitation was a convenient method for using DERA in synthesis. However, the cell free extracts usually produced similar results.

Using α-hydroxyaldehydes with different substitution at the β-position (3-position), a variety of sugars were produced. Due to DERA's selectivity for D-2-hydroxyaldehydes, a single diastereomer was isolated when racemic 3-thioglyceraldehyde (Compound 3) was used as acceptor. Compound 3 produced 2-deoxy-5-thio-D-erythropentose in 33 percent yield as a mixture of α- and β-anomers.

2-Deoxy-L-fucose (Compound 2a), was synthesized from Compound 1a which is available from the Sharpless asymmetric dihydroxylation [Henderson et al., *J. Am. Chem. Soc.*, 116:558 (1994)]. Dihydroxyaldehyde Compound 1b afforded the unusual sugar Compound 2b in an analogous manner.

When acetaldehyde is used as the donor and acceptor, the resulting β-hydroxyaldehyde cannot form an internal hemiacetal, which results in an aldehyde being available for a second aldol reaction with acetaldehyde. The aldehyde resulting from this second addition, 2,4,6-trideoxy-D-hexapyranoside Compound 5, exists as the hemiacetal and was isolated.

When α-substituted acetaldehydes are used that contain functionality that will not cyclize after the first aldol reaction, the products from the sequential aldol reaction then cyclize in the pyranose form, stopping the polymerization after the addition of two acetaldehyde monomers. In this manner, 2,4-dideoxyhexoses with various substituents at the six position (Compounds 6–8) were also obtained [Gijsen et al., *J. Am. Chem, Soc.*, 116:8422 (1994)].

Materials and Methods

Fast Protein Liquid Chromatography was performed on a Pharmacia FPLC system with columns purchased from Pharmacia. SDS-PAGE and IEF were performed with a Pharmacia PhastSystem instrument, using preformulated gels from the same company. UV and visible spectroscopy were obtained with a Beckman DU-70 Spectrophotometer at 25° C. NMR spectra were obtained on Bruker AMX-400 or AMX-500 spectrometers. High resolution mass spectra (HRMS) were obtained on a VG ZAB-ZSE Mass Spectrometer in electron impact (EI), fast atom bombardment (FAB), or with solid probe. All chemicals and enzymes, except DERA, were purchased from Aldrich, Sigma or Cambridge Isotope Laboratories.

EXAMPLE 1

Preparation of the Enzyme, DERA

The enzyme "DERA", 2-deoxyribose-5-phosphate aldolase was obtained by recombinant methods that follow:

A. Preparation of cell-free extract using lysozyme

To a suspension of *E. coli* cells strain DH5α (ATCC 86963), in Tris buffer (8 mL/g cells, 50 mM, pH 8.0), were added EDTA 50 mM, pH 8.2), and lysozyme (2 mg/g cells). The suspension was gently stirred at room temperature for one hour, and the suspension kept at 4° C. overnight. The preparation was gently sonicated for 20 minutes to decrease viscosity. DNase (10 µg/g cells) and $MgCl_2$ (0.95 µg per mL of preparation) were added and the mixture refrigerated for 20 minutes. The mixture was then centrifuged for 30 minutes at 16000×g, and the supernatant was used in the next purification steps.

In order to assess the efficiency of the above method, a cell-free extract was prepared by disruption of the above *E. coli* cells in a French Press. Five grams of cells were suspended in Tris buffer (45 mL, 50 mM, pH 8.0) and lysed twice in a French Press at 16,000 lb/in. After centrifugation for 30 minutes at 16,000×g, total proteins and DERA activities were measured in the supernatant and found to be similar to DERA activities in cell-free extracts obtained by the lysozyme method.

B. Purification of DERA

Streptomycin sulfate was added at 4° C. with stirring to the cell-free extract obtained by digestion of the cells with lysozyme until a concentration of 1 percent was obtained, and stirring was continued for 20 minutes. The solution was then centrifuged for 30 minutes at 16,000×g. The supernatant collected and ammonium sulfate added at 4° C. with stirring until a concentration of 40 percent ammonium sulfate saturation was obtained. The solution was then centrifuged for 30 minutes at 16,000×g, the supernatant collected and ammonium sulfate added at 4° C. with stirring until the ammonium sulfate saturation was raised to 65 percent. The solution was then centrifuged for 30 minutes at 16,000×g and the resulting pellet resuspended in Tris buffer (100 mM, pH 7.6), containing 2 mM EDTA (Buffer A). This solution was desalted using Centriprep™ tubes (Amicon). Further purification was achieved by FPLC at room temperature.

C. Anion exchange chromatography

Anion exchange chromatography was performed on a Mono Q™ column 10/10 with about 150 mg of protein loaded on the column in each run. The sample was eluted with a gradient of 1M NaCl in 200 mL of buffer A. Fractions (4 mL) containing protein were detected by absorbance at 280 nm, the active fractions pooled and the buffer exchanged with the initial buffer of the chromatofocusing using Centriprep tubes.

D. Chromatofocusing

Chromatofocusing was performed on a Mono P™ column 5/20 using two different pH gradients: 6 to 4 and 5.5 to 4.5. For the gradient from pH 6 to pH 4, the initial buffer was Bis-Tris (25 mM, adjusted to pH 6.3 with HCl). The elution buffer was Polybuffer 7-4 (adjusted to pH 4 with HCl), diluted by a factor of ten with distilled water. For the gradient from pH 5.5 to pH 4.5, the initial buffer was piperazine (25 mM, pH 6.3, and the elution buffer was prepared as before with a final pH of 4.5. In both cases, before loading the sample, a pregradient was made by washing the column with 3 mL of the elution buffer. The separation was optimized by loading 100 µg of protein in a total volume of 100 µL. To scale up the process, 15 mg of protein were applied in each run, and the protein fractions (0.5 mL each) were monitored by absorbance at 280 nm.

E. Determination of enzyme purity

Fractions obtained from different columns were analyzed by SDS-PAGE (sodium dodecyl sulfate-polyacrylamide gel electrophoresis) and isoelectrofocusing (IEF). For SDS-PAGE, preformulated gels were used with a gradient (from 8 to 25 percent) of polyacrylamide in the separating zone. Prior to electrophoresis, the samples were boiled at 100° C. for 3 minutes in a solution containing 0.5 percent sodium dodecyl sulfate and 5 percent 2-mercaptoethanol. The IEF was performed on preformulated gels with a pH range from 4.5 to 6.5. In both cases, the markers used were from Pharmacia. The gels were stained using the Pharmacia PhastSilver™ Kit, modified to provide higher sensitivity. This technique can detect proteins in the range of 0.1 to 0.05 ng of protein per band [Heukeshoven et al., at *Electrophoresis*, 9:28 (1988)].

F. Enzymatic assay

DERA activity was assayed with a coupled enzymatic system where 0.5 mM of 2-deoxyribose-5-phosphate, 0.12 mM NADH, and a mixture of glycerophosphate dehydrogenase and triose phosphate isomerase were incubated in triethanolamine buffer (50 mM, pH 7.5) at 25° C. The assay was initiated by addition of DERA, and the decrease in the absorbance at 340 nm was monitored. The extinction coefficient for NADH was taken as $6.22 \times 10^3$ $M^{-1}cm^{-1}$. Protein concentration was measured by the Bradford assay using the Coomasie Plus Kit Reagent from Pierce Co., instead of the method described previously [Bradford, *Anal. Biochem*, 72:248 (1976) (describing the Bradford assay); Barbas et al., *J. Am. Chem. Soc.*, 112:2013 (1990) (describing the previous method); Chen et al., *J. Am. Chem. Soc.*, 114:741 (1992) (describing the previous method)].

EXAMPLE 2

DERA-catalyzed Synthesis of 2-deoxy-L-fucose (Compound 2a)

The acceptor aldehyde (2S,3R)-dihydroxybutyraldehyde (Compound 1a) was obtained by the Sharpless asymmetric dihydroxylation of butyraldehyde. Henderson et al., *J. Am. Chem. Sox.*, 116:58 (1994). Compound 1a (41.3 mg, 0.40 mmol) and acetaldehyde (52.8 mg, 1.2 mmol) were dissolved in 1 mM Tris and 0.01 mM EDTA buffer (4 mL, pH 7.3), and 160 units of DERA were added. The resulting solution was stirred in the dark for two days under nitrogen atmosphere. The reaction was quenched by addition of two volumes of acetone, cooling to 0° C. for 20 minutes, and centripred to remove the precipitated protein. The solvent was removed under reduced pressure. The product, 2-deoxyfucose (also known as 2,6-dideoxy-L-lyxo-hexose, Compound 2a), (36 mg, 51 percent) was purified by silica gel column chromatography (10:2, $CHCl_3$/MeOH). The $^1H$ NMR spectra was identical to that reported in the literature. DeBruyn et al., *Acta Chem. Scand., Ser. B B*30(9) :820 (1976).

EXAMPLE 3

Use of DERA to prepare 2-Deoxy-5-phenyl-L-lyxopentose (Compound 2b)

The enzyme, DERA was obtained as described in Example 1. The sharpless asymmetric dihydroxylation method was used to prepare 3-(3-phenyl-1R,2S-dihydroxypropyl-1,5-dihydro-3H-2,4-benzodioxepine. Henderson, et al, *J. Am. Chem. Soc.*, 116:558(1994).

A solution of 3-(3-phenyl-1R,2S-dihydroxypropyl)-1,5-dihydro-3H-2,4-benzodioxepine (200 mg, 0.70 mmol) in 0.1N HCl (7 mL) was heated at 70° C. for three hours to form 3-phenyl-2S,3R)-dihydroxypropionaldehyde (Compound 1b). The solution was cooled to room temperature and the pH adjusted to 7.5. Acetaldehyde (0.12 mL, 2.1 mmol) and DERA (280 Units) were added and the solution maintained at 25° C. in the dark for two days. Purification by silicagel column chromatography ($CHCl_3$/MeOH, 2:1) afforded Compound 2b (67 mg, 46 percent yield) as a thick oil. $^1H$ NMR (400 MHz, $CD_3OD$) δ 1.36 (dd, J=4.9, 15.1 Hz, 1H), 1.45 (dd, J=5.2, 15.1 Hz, 1H), 3.40 (m, 1H), 3.58 (d, J=5.0 Hz, 1H), 3.71 (dd, J=4.0, 5.2 Hz, 1H), 5.10 (d, J=3.1 Hz, 1H), 7.27–7.44 (m, 5H); $^{13}C$ NMR (100 MHz, $CD_3OD$) δ 40.35, 62.90, 73.50, 73.94, 106.65, 127.80, 128.17, 128.54, 128.63, 129.15, 140.81; HRMS for $C_{11}H_{14}O_4$ (M+Na$^+$), calculated to be 233.0790, and found to be 233.0779.

EXAMPLE 4

Use of DERA to Prepare 2-Deoxy-5-thio-D-erythro-pentose (Compound 4)

The acceptor aldehyde, 3-thioglyceraldehyde (Compound 3), was prepared by the method of Effenberger. [Effenberger *Tetrahedron Lett.*, 33:5157 (1992)]. DERA (400U) was added to a 10 mL solution containing the acceptor aldehyde (100 mM Compound 3) and donor aldehyde (300 mM acetaldehyde), triethanolamine buffer (100 mM, pH 7.3) and EDTA (1 mM). This reaction is shown in Scheme 1. The resulting solution was stirred in the dark for 2 days under a $N_2$ atmosphere. The reaction was quenched by addition of 2 volumes of acetone and cooling to 0° C. for 20 minutes. The precipitated protein was removed by centrifugation. After removal of the solvent under reduced pressure, a 33 percent yield of Compound 4 was obtained (characterized as 2-deoxy-5-thio-1,3,4-tri-O-acetyl-D-erythro-pentose). Compound 4 was purified from the residue by preparative TLC on silica (methanol/chloroform/hexane, 1:90:10).

The α-anomer was obtained in 15 percent yield (41 mg,$R_f$=0.27). $^1H$ NMR (500 MHz, $CDCl_3$) δ 2.06 (s, 3H), 2.09 (s, 3H), 2.13 (s, 3H), 2.29 (ddd, J=2.8, 3.8, 15.4 Hz, 1H), 2.50 (dd, J=3.8, 12.8 Hz, 1H), 2.63 (ddd, J=3.2, 4.4, 15.4 Hz, 1H), 3.36 (dd, J=11.1, 12.8 Hz, 1H), 5.12 (ddd, J=2.6, 3.9, 11.1 Hz, 1H) 5.22–5.25 (m, 1H), 5.79 (t, J=3.5 Hz, 1H); $^{13}C$ NMR (125 MHz, $CDCl_3$) δ 20.87, 20.97, 21.09, 22.73, 35.87, 67.39, 68.84, 70.18, 169.25, 169.83, 170.09; HRMS for $C_{11}H_{16}O_6S$ (M+Na$^+$), calculated 299.0565, found 299.0565.

The β-anomer was obtained in 18 percent yield (50 mg, $R_f$=0.36). $^1H$ NMR (500 MHz, $CDCl_3$) δ 2.05 (s, 3H), 2.12 (s, 3H), 2.08–2.15 (m, 1H), 2.16 (s, 3H), 2.44 (ddd, J=2.9, 11.3, 13.6 Hz, 1H), 2.87 (dd, J=1.6, 14.6 Hz, 1H), 3.26 (dd, J=1.9, 14.6 Hz, 1H), 5.21 (ddd, J=3.8, 3.8, 11.3 Hz, 1H), 5.34 (ddd, J=1.6, 1.9, 3.8 Hz, 1H), 6.03 (br s, 1H); $^{13}C$ NMR (125 MHz, $CDCL_3$) δ 21.0, 21.1, 21.2, 28.4, 32.5, 66.1, 67.3, 72.4, 169.4, 170.1, 170.4; HRMS for $C_{11}H_{16}O_6S$ (M+Na$^+$), calculated 299.0565, found 299.0577.

General Procedure for DERA-catalyzed multiple reactions

DERA (1000U) was added to a 20 ml. solution containing 100 mM of acceptor aldehyde and 300 mM of donor aldehyde, 100 mM triethanolamine buffer (pH 7.3) and 1 mM EDTA. The resulting solution was stirred in the dark for 6 days under $N_2$. The reaction was quenched by addition of 2 volumes of acetone, then cooled to 0° C. for 20 minutes and centrifuged to remove the precipitated protein. After removal of the solvent under reduced pressure, the residue was purified by silica gel chromatography.

EXAMPLE 5

Use of DERA to Prepare 2,4,6-Trideoxy-D-erythrohexose (Compound 5)

The reaction was performed according to the general procedure for multiple reactions using DERA, as described above, where both the donor and acceptor aldehydes were acetaldehyde. The crude product was purified by flash chromatography (silica, ethyl acetate) to give Compound 5 (60 mg, 22 percent yield) as a mixture of anomers (α:β ratio in $D_2O$ 1:8).

$^1H$ NMR (400 MHz, $CDCl_3$) δ 1.21 (d, J=6.3 Hz, 3H, α), 1.23 (d, J=6.3 Hz, 3H, β), 1.42–2.00 (m, 4H), 3.09 (d, J=6.2 Hz, 1H, α), 3.43 (d, J=5.1 Hz, 1H, β), 4.07 (ddq, J=2.2, 6.3, 11.4 Hz, 1H, β), 4, 17 (s, 1H), 4.18 (s, 1H), 4.18–4.24 (m, 1H, α), 4.32 (dq, J=2.7, 5.4 Hz, 1H, β), 4.42 (ddq, J=2.3, 6.3, 11.8 Hz, 1H, α), 5.16 (br d, J=10.2 Hz, 1H, β), 5.32 (t, J=4.8 Hz, 1H, α); α-anomer: $^{13}C$ NMR (100 MHz, $CDCl_3$) δ 21.43, 34.90, 39.86, 59.00, 65.02, 92.25; β-anomer: $^{13}C$ NMR ($CDCl_3$) δ 21.31, 39.42, 39.55, 65.59, 66.57, 92. HRMS for $C_6H_{12}O_3$ (M+Na$^+$), calculated 155.0684, found 155.0684.

EXAMPLE 6

Use of DERA to Prepare 6-O-Methyl-2,4-dideoxy-D-erythro-hexose (Compound 6)

The reaction was performed according to the general procedure for multiple reactions using DERA, as described above, where the acceptor aldehyde was 2-methoxyacetaldehyde and the donor aldehyde was acetaldehyde. The crude product was purified by flash chromatography (silica, ethyl acetate to ethyl acetate/methanol 12:1) to give Compound 6 (211 mg, 65 percent yield) as a mixture of anomers (α:β ratio in $D_2O$ 1:7).

$^1H$ NMR (400 MHz, $CDCl_3$) δ 1.45–1.97 (m, 4H), 3.35 (s, 3H, β), 3.36 (s, 3H, α), 3.35–3.46 (m, 2H), 4.08–4.15 (m, 1H, β), 4.17–4.20 (m, 1H, α), 4.28–4.32 (m, 1H, β), 4.42–4.49 (m, 1H, α), 5.14 (dd, J=2.2, 9.8 Hz, 1H, β), 5.34 (d, J=3.3 Hz, 1H, α) ; α-anomer: $^{13}$C NMR (100 MHz, CDCl$_3$) δ 34.11, 34.81, 59.08, 62.23, 64.35, 75.54, 92.14; β-anomer: $^{13}$C NMR (100 MHz, CDCl$_3$) δ 33.83, 39.30, 59.05, 64.88, 69.51, 75.76, 92.70; HRMS for C$_7$H$_{14}$O$_4$ (M+Na$^+$), calculated 185.0790, found 185.0796.

EXAMPLE 7

Use of DERA to Prepare 6-Chloro-2,4,6-trideoxy-D-erythro-hexose (Compound 7)

The reaction was performed according to the general procedure for multiple reactions using DERA, described above, where the acceptor aldehyde was 2-chloroacetaldehyde and the donor aldehyde was acetaldehyde. The crude product was purified by flash chromatography (silica, ethyl acetate/hexane from 2:1 to 3:1) to give Compound 7 (235 mg, 70 percent yield) as a mixture of anomers (α:β ratio in D$_2$O 1:6).

$^1$H NMR (400 MHz, CDCl$_3$) δ 1.53–2.00 (m, 4H) 3.52–3.62 (m, 2H), 4.12–4.18 (m, 1H, β), 4.23–4.28 (m, 1H, α), 4.34–4.38 (m, 1H, β), 4.45–4.52 (m, 1H, α), 5.20 (dd, J=2.1, 9.5 Hz, 1H, β), 5.37 (br t, J=4.1 Hz, 1H, α) ; α-anomer: $^{13}$C NMR (100 MHz, CDCl$_3$) δ 35.07, 39.23, 47.03, 63.24, 64.89, 92.54; β-anomer: $^{13}$C NMR (100 MHz, CDCl$_3$) δ 34.74, 35.35, 47.75, 64.49, 70.50, 93.03; HRMS for C$_6$H$_{11}$O$_3$Cl (M+Na$^+$), calculated 189.0294, found 189.0288.

EXAMPLE 8

Use of DERA to prepare 6-Azido-2,4,6-trideoxy-D-erythro-hexose (Compound 8)

The reaction was performed according to the general procedure for multiple reactions using DERA, as described above, where the acceptor aldehyde was 2-azidoacetaldehyde and the donor aldehyde was acetaldehyde. The crude product was purified by flash chromatography (silica, ethyl acetate/hexane from 1:1 to 2:1) to give Compound 8 (81 mg, 23 percent yield) as a mixture of anomers (α:β ratio 2:3).

$^1$H NMR (400 MHz, D$_2$O) δ 1.54–1.98 (m, 4H), 3.37–3.51 (m, 2H), 4.09–4.16 (m, 1H, β), 4.42–4.27 (m, 1H, α), 4.35–4.39 (m, 1H, β), 4.41–4.48 (m, 1H, α), 5.15 (dd, J=2.0, 10.0 Hz, 1H, β), 5.31 (br t, J=2.2 Hz, 1H, α); α-anomer: $^{13}$C NMR (100 MHz, D$_2$O) δ 36.02, 37.64, 56.49, 65.61, 66.44, 94.01; β-anomer: $^{13}$C NMR (100 MHz, D$_2$O) δ 35.94, 40.46, 56.69, 66.98, 72.55, 94.44; HRMS for C$_6$H$_{11}$O$_3$N$_3$ (M+Na$^+$), calculated 196.0698, found 196.0706.

The foregoing description and the examples are intended as illustrative and are not to be taken as limiting. Still other variations within the spirit and scope of this invention are possible and will readily present themselves to those skilled in the art.

We claim:

1. A process for using 2-deoxyribose-5-phosphate aldolase (DERA) to prepare a pentose product of Formula I

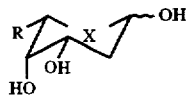

wherein X is O, and R is C$_1$–C$_4$ alkyl or phenyl that comprises the steps of:

(a) admixing an aldehyde of Formula II

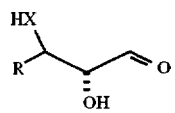

wherein X and R are as defined above and the configuration of the carbon to which R and HX are bonded is S, with acetaldehyde and DERA in an aqueous medium at a pH value of about 6.5 to about 8.5 and at a temperature of about 5° C. to about 45° C. to form a reaction mixture;

(b) maintaining said reaction mixture at said temperature and pH value for a time period sufficient for said pentose product to form; and (c) recovering said pentose product.

2. The process according to claim 1 wherein said acetaldehyde is present in stoichiometric excess over the aldehyde of Formula II.

3. The process according to claim 1 wherein said maintenance step is carried out in the absence of light.

4. The process according to claim 1 wherein said temperature is about 15° C. to about 35° C.

5. A process for using 2-deoxyribose-5-phosphate aldolase (DERA) to prepare a 2-deoxy-5-substituent-L-lyxo-pentose product in which the 5-substituent is C$_1$–C$_4$ alkyl or phenyl comprising the steps of:

(a) admixing an aldehyde of Formula III

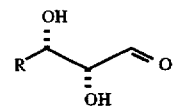

wherein R is C$_1$–C$_4$ alkyl or phenyl, with acetaldehyde and DERA in an aqueous medium at a pH value of about 6.5 to about 8.5 and at a temperature of about 5° C. to about 45° C. to form a reaction mixture;

(b) maintaining said reaction mixture at said temperature and pH value for a time period sufficient for said product to form; and (c) recovering said product.

6. The process according to claim 5 wherein said acetaldehyde is present in stoichiometric excess over the aldehyde of Formula III.

7. The process according to claim 5 wherein said maintenance step is carried out in the absence of light.

8. The process according to claim 5 wherein pH value is about 7 to about 8.

9. The process according to claim 5 wherein said temperature is about 15° C. to about 35° C.

10. A process for using 2-deoxyribose-5-phosphate aldolase (DERA) to prepare a 2-deoxy-5-substituent-L-lyxo-pentose product in which the 5-substituent is C$_1$–C$_4$ alkyl or phenyl comprising the steps of:

(a) admixing an aldehyde of Formula III

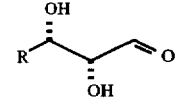

wherein R is C$_1$–C$_4$ alkyl or phenyl, with acetaldehyde and DERA in an aqueous medium at a pH value of about 7 to about 8 at a temperature of about 15° C. to about 35° C. to form a reaction mixture in which acetaldehyde is in stoichiometric excess over the aldehyde of Formula III;
(b) maintaining said reaction mixture in the absence of light at said temperature and pH value for a time period sufficient for said product to form; and
(c) recovering said product.

11. The process according to claim 10 wherein R is methyl.

12. The process according to claim 10 wherein R is phenyl.

13. A process for using 2-deoxyribose-5-phosphate aldolase (DERA) in a single vessel synthesis of a product compound of Formula V

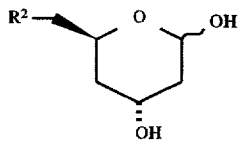

V wherein $R^2$ is selected from the group consisting of hydrogen, $C_1$-$C_4$ alkoxy, halo and azido groups, that comprises the steps of:
(i) admixing the following materials in an aqueous medium at a pH value of about 6.5 to about 8.5 at a temperature of about 5° C. to about 45° C. in a single reaction vessel to form a reaction mixture:
(a) acetaldehyde donor
(b) $R^2$-substituted acetaldehyde acceptor,
(c) DERA wherein the molar ratio of donor to acceptor is about 2:1 to about 4:1 and DERA is present in an amount of about 125 to about 150U per millimole of donor and acceptor combined;

(ii) maintaining said admixture at said temperature and pH value for a time period sufficient for said product compound to form; and (iii) recovering said product compound.

14. The process according to claim 13 wherein said maintenance step is carried out in the absence of light.

15. The process according to claim 13 wherein pH value is about 7 to about 8.

16. The process according to claim 13 wherein said temperature is about 15° C. to about 35° C.

* * * * *